(12) United States Patent
Howlett

(10) Patent No.: US 6,170,482 B1
(45) Date of Patent: Jan. 9, 2001

(54) INHALATION APPARATUS

(75) Inventor: David Howlett, Kings Lynn (GB)

(73) Assignee: Bespak plc (GB)

(*) Notice: Under 35 U.S.C. 154(b), the term of this patent shall be extended for 0 days.

(21) Appl. No.: 09/031,667

(22) Filed: Feb. 27, 1998

(30) Foreign Application Priority Data

Mar. 3, 1997 (GB) .................................................. 9704361

(51) Int. Cl.$^7$ .................................................. A61M 11/00
(52) U.S. Cl. .................. 128/200.23; 128/200.14
(58) Field of Search .................. 128/203.15, 203.12, 128/200.14, 200.23, 200.24, 204.25, 203.19–203.25, 200, 200.18, 205.24

(56) References Cited

U.S. PATENT DOCUMENTS

| | | |
|---|---|---|
| 4,592,348 | 6/1986 | Waters, IV et al. . |
| 4,852,561 * | 8/1989 | Sperry ............................ 128/200.23 |
| 4,940,051 * | 7/1990 | Lankinen ........................ 128/203.15 |
| 5,040,527 | 8/1991 | Larson et al. . |
| 5,178,138 * | 1/1993 | Walstrom et al. ............... 128/200.23 |
| 5,447,150 * | 9/1995 | Bacon .............................. 128/200.23 |
| 5,598,836 * | 2/1997 | Larson et al. ................... 128/200.14 |
| 6,082,355 * | 7/2000 | Howlett ........................... 128/200.23 |

FOREIGN PATENT DOCUMENTS

| | | | |
|---|---|---|---|
| 0147028 | 7/1985 | (EP) . | |
| 1021739 | 3/1966 | (GB) . | |
| 2061116 | 5/1981 | (GB) . | |
| 2104393 * | 8/1982 | (GB) | ............................ 128/200.23 |
| 2279879 | 1/1995 | (GB) . | |

* cited by examiner

Primary Examiner—Aaron J. Lewis
Assistant Examiner—Teena Mitchell
(74) Attorney, Agent, or Firm—Smith, Gambrell & Russell, LLP

(57) ABSTRACT

This invention relates to an inhalation apparatus for dispensing substances for inhalation and, in particular, but not exclusively, for dispensing medicinal products in aerosol form from a pressurized dispensing container. The inhalation apparatus comprises an inhaler apparatus for dispensing a product comprising a housing having a portion adapted to receive a pressurized dispensing container of a product and a mouthpiece. The apparatus further comprises duct means communicating with the container, said duct means having an outlet defining the direction of flow of the product towards the mouthpiece section. Air inlet valve means are provided comprising at least one air inlet for allowing air into the housing and an airflow controller is biased to seal said air inlet. The airflow controller is manually movable to unseal the air inlet to allow air to flow into the housing when a user applies suction to the mouthpiece. Passage means are provided to direct the airflow to a location adjacent the outlet of the duct means and the positioning of the passage means relative to the duct means outlet and the mouthpiece is such that a component of the initial air flow direction opposes the product flow before being directed towards the mouthpiece.

6 Claims, 2 Drawing Sheets

INHALATION APPARATUS

This invention relates to an inhalation apparatus for dispensing substances for inhalation and, in particular, but not exclusively, for dispensing medicinal products in aerosol form from a pressurised dispensing container.

In known metered dose inhalers, the aerosol stream from a pressurised dispensing container is fired towards a patient or user of the inhaler into an airflow travelling in the same direction. In known devices, a user inhales through a mouthpiece of the inhaler and creates an airflow through the container from air inlet holes which are generally at a part of the inhaler well spaced from the mouthpiece. The medicament is then released into this airflow at a point between the air inlet holes and the mouthpiece so that it is travelling in the same direction as the airflow. Typically, in such devices, there is no restriction in the airflow between the air inlet holes and the mouthpiece. Because of this, a substantial airflow may be created by a user of the device and, because the medicament is fired into the airflow in the same direction as the airflow, the effect is that particles of medicament can obtain quite substantial velocities. As inhalers of this type are normally designed to be as small as practical for the convenience of users, the distance between the point at which the medicament is fired into the airflow and the patient's mouth is usually quite small, so that there is little distance to reduce the inertia of particles of medicament with the result that the particles may impact in the oropharynx of a user with quite high velocity. This can be a problem with some medicaments. It is also known to provide a sensor in an inhalation apparatus to detect inhalation by the user in order to synchronise with inhalation the release into the inhaled airflow of the substance to be inhaled. It is, for example, important in the administration of aerosol products for the relief of asthma that the timing of the dispensing operation should be carefully controlled to ensure maximum deposition of substance in the user's lungs.

It is known from GB-A-226 6466 to provide an electrically operated dispensing means responsive to a signal generated by a sensor which is responsive to a flow of air through a passageway. A disadvantage of this solution is that the apparatus is expensive.

In an effort to overcome these problems, devices have been produced in which the medicament is fired into a holding volume which allows the velocity of the medicament to be reduced and also allows some evaporation to occur.

However, these devices with a holding volume tend to be of significantly larger size than the standard metered dose inhalers and, therefore, less convenient and attractive to users.

One solution proposed in GB-A-2279879 uses a reverse flow. In this inhaler, the air inlets are provided at a location axially between the air outlet of the duct means connecting an outlet of the container with the mouthpiece and the mouthpiece, and a passage is provided connecting the inlets to a location adjacent to the outlet of the duct means. Thus, when a user inhales through the mouthpiece, an airflow is created from the inlet means to the mouthpiece, the airflow having a component directed away from the mouthpiece towards the outlet of the duct means.

An object of the present invention is to provide an inhaler which allows delivery of medicament to the user at reduced velocity without significantly increasing the size of the inhaler. Additionally, another object is to provide an inhaler which coordinates the discharge of the medicament with the inhalation cycle of the user in order to optimise the deposition of the medicament in the user's lungs.

The present invention therefore provides a housing having a portion adapted to receive a pressurised dispensing container of a product and a mouthpiece, said apparatus further comprising duct means communicating with the container, said duct means having an outlet defining the direction of flow of the product towards the mouthpiece section, air inlet valve means comprising at least one air inlet for allowing air into the housing and an airflow controller biased to seal said air inlet, said airflow controller being manually movable to unseal the air inlet to allow air to flow into the housing when a user applies suction to the mouthpiece, passage means being provided to direct the airflow to a location adjacent the outlet of the duct means, the positioning of the passage means relative to the duct means outlet and the mouthpiece being such that a component of the initial air flow direction opposes the product flow before being directed towards the mouthpiece.

An advantage of the present inhaler is that medicament is delivered to a user in the action of inhaling, allowing a greater proportion of the medicament to be deposited in the user's lungs. Also the dispensed medicament is slowed and mixed by the reverse flow of air away from the mouthpiece, towards the opening of the duct means, and the vortex created, decreasing the chance of damage to the user's throat and increasing the amount of medicament deposited in the user's lungs.

Preferably the housing comprises a partition separating the housing into an upper cylindrical portion for receiving a dispensing container and a lower portion for receiving the airflow controller, wherein the air inlet is located in the partition and the airflow controller has a movable actuator for sealing the air inlet.

Preferably the airflow controller comprises a spring biasing the actuator into contact with the partition.

Preferably the actuator has an extended member which projects into the upper portion of the housing and which, in use, is contacted by the container.

Preferably the passage means comprises a passage formed between an extension of the mouth piece and a support means surrounding the duct means configured to direct the flow of air there through with a component of its velocity towards the duct outlet.

A preferred embodiment of the present invention will now be described, by way of example only, with reference to the accompanying drawings of which:

Figure 1:
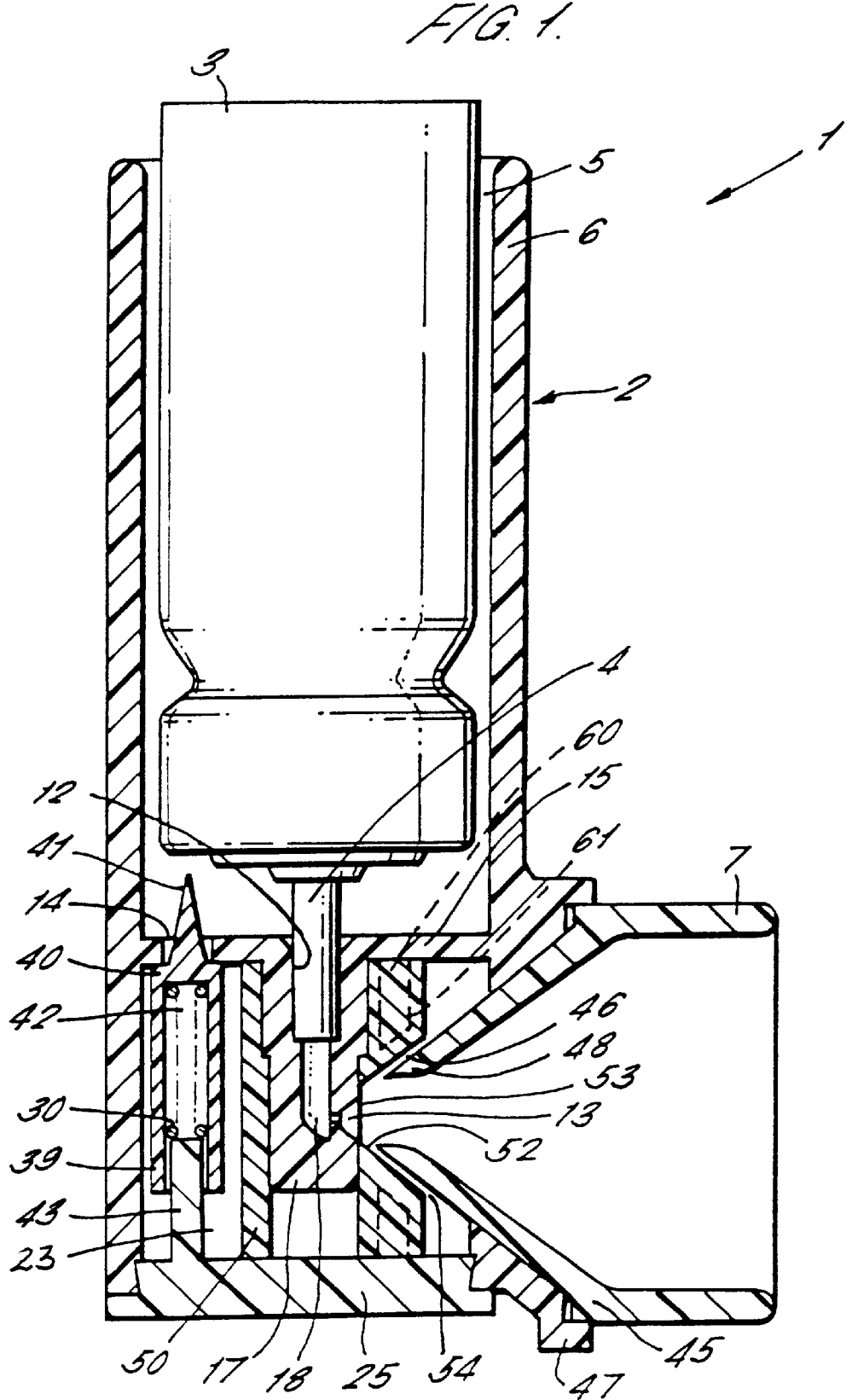
FIG. 1 is a sectional view of the inhalation apparatus.

The inhalation apparatus 1 of FIG. 1 comprises a generally cylindrical housing 2, open at its upper end to allow air into the apparatus 1 and to receive a cylindrical pressurised dispensing container 3. The housing 2 consists of a cylindrical portion 6 which receives the container 3 and a mouthpiece 7 projecting laterally from the lower end of the cylindrical portion 6. With the container 3 inserted in the cylindrical portion 6 there exists a space 5 between the container 3 and the inside surface of the cylindrical portion 6 adequate to allow air flow there through. The cylindrical portion 6 is divided into an upper and a lower section by an annular partition 15. Projecting from a lower side of the partition 15 is an elongate annular socket 17 defining a central bore 12 for receiving a valve stem 4 of the dispensing container 3.

The valve stem receiving bore 12 communicates via a duct 18 with an aperture 13 in the side wall of the annular socket 17 which is arranged to direct an aerosol spray through 90° on discharge through the valve stem receiving bore 12 into the mouthpiece 7.

The socket 17 is surrounded by a support member 50. The support member 50 is of a generally cylindrical form and engages with the socket 17 in an air-tight manner. The support member 50 has a tapered bore 52 in a side wall thereof, the narrow end of which communicates with the aperture 13. The bore 52 has a relatively wide exit 54 for receiving an end of the mouthpiece 7.

The mouthpiece 7, which may be generally circular or mouth-shaped, is connected to the rest of the housing 2 via a generally frusto-conical extension 45 of the mouthpiece 7. The mouthpiece extension 45 is push-fitted into a frusto-conical socket 47 located on the housing 2. Alternatively, the mouthpiece 7 may be integrally bonded to the rest of the housing 2. When the mouthpiece extension 45 is inserted into the socket 47, the distal end 48 of the extension 45 partially extends into the tapered bore 52. A restricted airflow passage 46 is formed between the proximate surfaces of the extension 45 and the walls of the bore 52, directed towards the aperture 13 of the socket 17.

The lower section of the cylindrical portion 6 of the housing 2 defines a chamber 23 in which is located the socket 17 and support member 50. The chamber 23 is closed by an end cap 25. The end cap 25 is push-fitted onto the end of the housing 2. Alternatively, the end cap may be bonded to the tubular portion 6 of the housing 2. The socket support 50 extends axially between the lower surface of the partition 15 and the upper surface of the end cap 25. Thus, the presence of the end cap 25 prevents axial movement of the socket support 50. Raised lugs 60 projecting from the lower surface of the partition 15 and the upper surface of the end cap 25 engage respectively upper and lower recesses 61 in the socket support 50. Thus, rotational movement of the socket support 50 about the annular socket 17 is prevented and the opening 13 remains in alignment with the entrance 53 to the orifice 52.

Also located in the chamber 23 and projecting inwardly from the end cap 25 is a spring support 43 and spring operated valve 39.

The valve 39 comprises an actuator 40, having a generally conical head which extends upwardly from the valve 39 to engage with a vent hole 14 formed in the partition 15. The head 41 also extends into the upper section of the cylindrical portion 6 of the housing 2. A spring 30 is positioned between the spring support 43 and an upper end of a recessed bore 42 in the actuator 40 biasing the actuator 40 into sealing contact with the lower side of the partition 15 thereby closing the vent hole 14.

Figure 2:
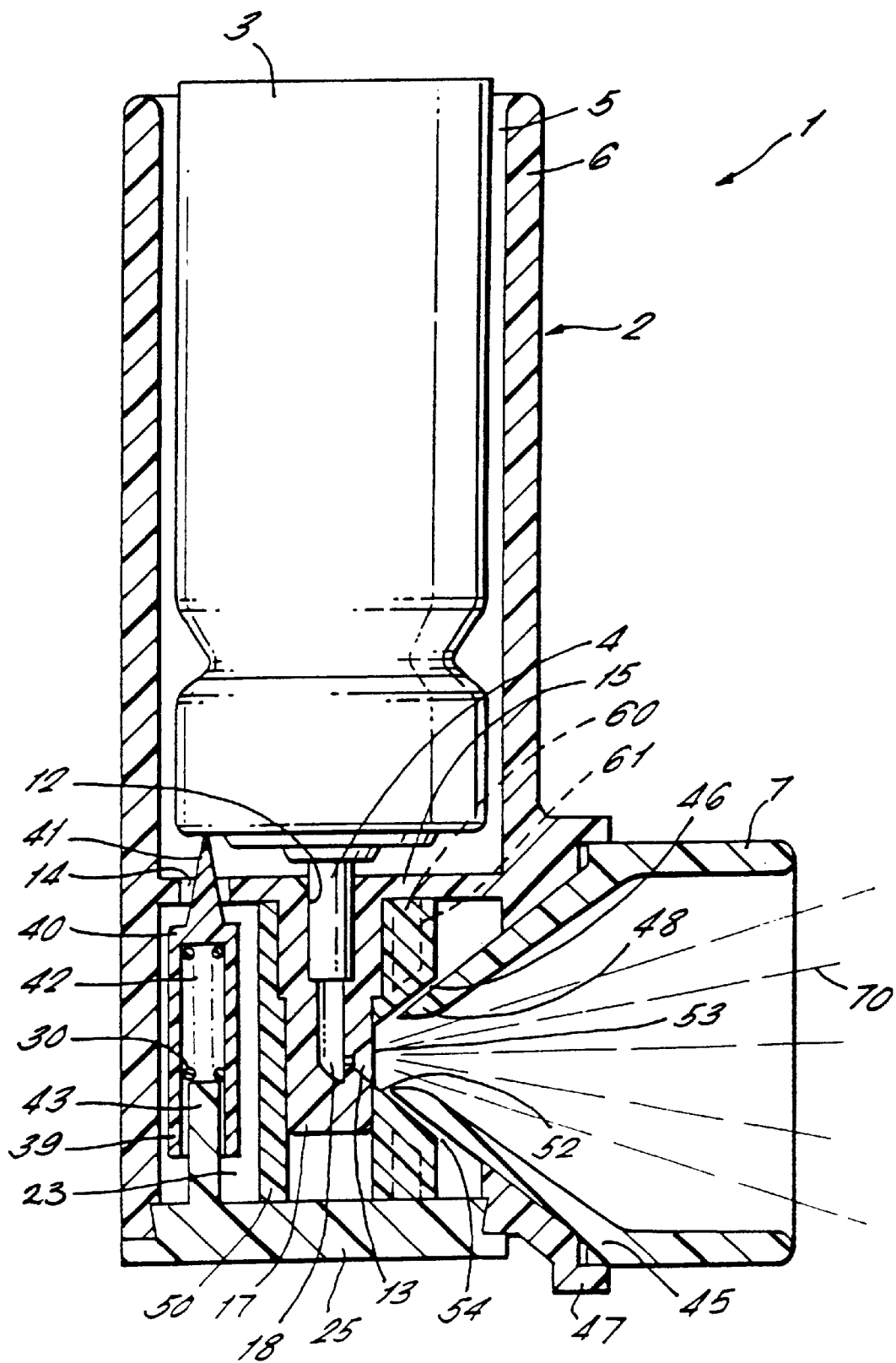
FIG. 2 is a sectional view of the inhalation apparatus in the operated state.

In operation the user inserts the mouthpiece 7 into his mouth and inhales. Initially, the valve 39 is closed and the vent hole 14 is sealed so that there is no airflow into the chamber 23. Whilst continuing to inhale, the user manually depresses the dispensing container 3 causing the dispensing container 3 to contact the valve head 41 and to push the valve actuator 40 downwardly as shown in FIG. 2. This causes the spring 30 to compress. Thus the actuator valve 40 moves out of contact with the vent hole 14 allowing the passage of air from the space 5 in the cylindrical portion 6, through the vent hole 14 and into the chamber 23. The air then circulates in the chamber 23, passing around the support member 50 before being drawn through the airflow passage 46 into the mouth piece 7 where it is inhaled. The air entering the mouthpiece 7 from the airflow passage 46 has a substantial component of its velocity directed towards the aperture 13.

Further depression of the dispensing container 3 causes the valve stem 4 of the dispensing container 3 to be depressed and a dose of medicament to be discharged from the dispensing container 3 via the valve stem 4 into the duct 18 and out through the aperture 13. The medicament is mixed with the air and a fine mist 70 is then inhaled by the user through the mouthpiece.

It will be appreciated that the airflow with which the dose of medicament is mixed has at least a component of its velocity directed in the opposite sense to the velocity of the medicament particles. The effect of this reverse airflow is to create a swirling airflow in the frusto-conical extension 45 which slows and mixes the discharged particles of medicament. The reverse flow component of the airflow and the vortex created ensure that the velocity of medicament particles is relatively low when they enter the oro-pharynx region of the patient.

It will also be appreciated that the stroke length of the valve stem 4 of the dispensing container 3 required to dispense a dose is such that the container 3 engages the extension 41 of the valve 39 and unseals the valve 40 from the vent hole 14 before the valve stem 4 is actuated to discharge medicament. Thus, the air inlet valve 39 ensures that the user begins to inhale before discharge of the medicament thus ensuring that a greater proportion of the discharged medicament is deposited correctly in the lungs of the user.

All of the components of the apparatus 1 may be plastics mouldings.

It will be appreciated that various modifications to the construction of the apparatus 1 may be made without departing from the scope of the invention.

What is claimed is:

1. An inhaler apparatus for dispensing a product comprising a housing having a portion adapted to receive a pressurized dispensing container of a product and a mouthpiece, said apparatus further comprising a duct communicating with the container, said duct having an outlet defining the direction of flow of the product towards the mouthpiece, an air inlet valve having an air inlet for allowing air into said housing and an airflow controller biased to seal said air inlet, said airflow controller being manually movable to unseal said air inlet to allow air to flow into said housing when a user applies suction to said mouthpiece, a passage which directs the airflow to a location adjacent said outlet of said duct, the positioning of said passage relative to said duct outlet and said mouthpiece being such that a component of the initial air flow direction is away from said mouthpiece and opposes the product flow before the air flows towards the mouthpiece.

2. An inhalation apparatus as claimed in claim 1 wherein said housing comprises a partition separating said housing into an upper cylindrical portion for receiving a dispensing container and a lower portion for receiving said airflow controller, wherein said air inlet is located in said partition and said airflow controller has a movable actuator for sealing said air inlet.

3. An inhalation apparatus as claimed in claim 2 in which said airflow controller comprises a spring biasing said actuator into contact with said partition.

4. An inhalation apparatus as claimed in claim 2 in which said actuator has an extended member which projects into said upper portion of said housing and which, in use, is contacted by the container.

5. An inhalation apparatus as claimed in claim 1 wherein said passage is located between an extension of said mouthpiece and a support member surrounding said duct, said passage being configured to direct the flow of the air therethrough with a component of air flow velocity directed towards the duct outlet.

6. A method of operating an inhalation apparatus comprising the steps of inserting a pressurized dispensing container into a housing; a valve stem of the dispensing container being received in an end of a duct, inserting a mouthpiece into the mouth and inhaling, wherein the flow of air is initially prevented by an airflow controller, but subsequent depressing of the dispensing container causes the airflow controller to allow air to flow into the mouthpiece and be inhaled and further depression of the dispensing container causes a dose of medicament to be dispensed via the valve stem and duct into the mouthpiece to mix with the inhaled air, the flow of air passing through a passage which directs a component of air flow velocity towards an opening of the duct.

* * * * *